US00PP22924P2

(12) United States Plant Patent
van der Velde

(10) Patent No.: US PP22,924 P2
(45) Date of Patent: Aug. 7, 2012

(54) *CHRYSANTHEMUM* PLANT NAMED 'ASTEC'

(50) Latin Name: *Chrysanthemum×morifolium*
Varietal Denomination: Astec

(75) Inventor: Hendrik W. van der Velde, Sliedrecht (NL)

(73) Assignee: Fleurations B.V., 's-Gravenzande (NL)

( * ) Notice: Subject to any disclaimer, the term of this patent is extended or adjusted under 35 U.S.C. 154(b) by 136 days.

(21) Appl. No.: 12/807,250

(22) Filed: Aug. 31, 2010

(51) Int. Cl.
*A01H 5/00* (2006.01)

(52) U.S. Cl. ..... Plt./294

(58) Field of Classification Search ..... Plt./294
See application file for complete search history.

*Primary Examiner* — June Hwu
(74) *Attorney, Agent, or Firm* — C. A. Whealy

(57) ABSTRACT

A new and distinct cultivar of *Chrysanthemum* plant named 'Astec', characterized by its daisy-type inflorescences with white-colored ray florets; strong and upright flowering stems; freely and uniform flowering habit; good postproduction longevity; and tolerance to White Rust.

2 Drawing Sheets

Botanical designation: *Chrysanthemum×morifolium.*
Cultivar denomination: 'ASTEC'.

BACKGROUND OF THE INVENTION

The present invention relates to a new and distinct cultivar of *Chrysanthemum* plant, botanically known as *Chrysanthemum×morifolium*, commercially grown as a cut flower and hereinafter referred to by the name 'Astec'.

The new *Chrysanthemum* plant is a product of a planned breeding program conducted by the Inventor in 's-Gravenzande, The Netherlands. The objective of the breeding program is to create new daisy-type *Chrysanthemum* plants with strong flowering stems, early flowering response, uniform flowering, attractive ray floret coloration and shape, excellent postproduction longevity and tolerance/resistance to pathogens.

The new *Chrysanthemum* plant originated from a cross-pollination made by the Inventor in 's-Gravenzande, The Netherlands in October, 2007, of a proprietary selection of *Chrysanthemum×morifolium* identified as code number Col 12, not patented, as the female, or seed, parent with a proprietary selection of *Chrysanthemum×morifolium* identified as code number Zl-1296, not patented, as the male, or pollen parent. The new *Chrysanthemum* plant was discovered and selected by the Inventor as a single flowering plant from within the progeny of the stated cross-pollination in a controlled greenhouse environment in 's-Gravenzande, The Netherlands in August, 2008.

Asexual reproduction of the new *Chrysanthemum* plant by terminal cuttings in a controlled greenhouse environment in 's-Gravenzande, The Netherlands since September, 2008, has shown that the unique features of this new *Chrysanthemum* plant are stable and reproduced true to type in successive generations.

SUMMARY OF THE INVENTION

Plants of the new *Chrysanthemum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Astec'. These characteristics in combination distinguish 'Astec' as a new and distinct *Chrysanthemum* plant:

1. Daisy-type inflorescences with white-colored ray florets.
2. Strong and upright flowering stems.
3. Freely and uniform flowering habit.
4. Good postproduction longevity; plants maintain good substance for about 19 days in an interior environment.
5. Tolerant to White Rust.

Plants of the new *Chrysanthemum* differ from plants of the female parent selection in the following characteristics:

1. Plants of the new *Chrysanthemum* are taller than plants of the female parent selection.
2. Plants of the new *Chrysanthemum* flower nine days later than plants of the female parent selection.
3. Plants of the new *Chrysanthemum* have larger inflorescences than plants of the female parent selection.

Plants of the new *Chrysanthemum* differ from plants of the male parent selection in the following characteristics:

1. Plants of the new *Chrysanthemum* are not as vigorous as plants of the male parent selection.
2. Plants of the new *Chrysanthemum* flower eight days earlier than plants of the male parent selection.
3. Plants of the new *Chrysanthemum* have smaller inflorescences than plants of the male parent selection.

Plants of the new *Chrysanthemum* can be compared to plants of *Chrysanthemum×morifolium* 'Bacardi', not patented. In side-by-side comparisons conducted in 's-Gravenzande, The Netherlands, plants of the new *Chrysanthemum* differed from plants of 'Bacardi' in the following characteristics:

1. Plants of the new *Chrysanthemum* had fewer whorls of ray florets than plants of 'Bacardi'.
2. Plants of the new *Chrysanthemum* had shorter ray florets than plants of 'Bacardi'.

3. Disc florets of plants of the new *Chrysanthemum* were darker green in color than disc florets of plants of 'Bacardi'.

BRIEF DESCRIPTION OF THE PHOTOGRAPHS

The accompanying colored photographs illustrate the overall appearance of the new *Chrysanthemum* plant. These photographs show the colors as true as it is reasonably possible to obtain in colored reproductions of this type. Colors in the photographs may differ slightly from the color values cited in the detailed botanical description which accurately describe the colors of the new *Chrysanthemum* plant.

The photograph on the first sheet comprises a side perspective view of a typical flowering stem of 'Astec' grown as a spray-type.

The photograph on the second sheet comprises close-up views of the upper (top of photograph) and lower surfaces (bottom of photograph) of typical inflorescences and leaves of 'Astec'.

DETAILED BOTANICAL DESCRIPTION

The aforementioned photographs and following observations and measurements describe plants grown during the spring and early summer in ground beds in a glass-covered greenhouse in 's-Gravenzande, The Netherlands under commercial practices. Plants were initially given twelve days of long day/short night treatments followed by short day/long night treatments to induce flower initiation and development. During the production of the plants, day temperatures ranged from 18° C. to 25° C., night temperatures ranged from 20° C. to 22° C. and light levels were about 5,000 lux. Plants were 8.5 weeks old when the photographs and the description were taken. In the following description, color references are made to The Royal Horticultural Society Colour Chart, 2007 Edition, except where general terms of ordinary dictionary significance are used.

Botanical classification: *Chrysanthemum×morifolium* 'Astec'.

Parentage:

*Female, or seed, parent*.—Proprietary selection of *Chrysanthemum×morifolium* identified as code number Col 12, not patented.

*Male, or pollen, parent*.—Proprietary selection of *Chrysanthemum×morifolium* identified as code number Zl-1296, not patented.

Propagation:

*Type*.—Terminal vegetative cuttings.

*Time to initiate roots, summer*.—About four days at 20° C.

*Time to initiate roots, winter*.—About six days at 20° C.

*Time to produce a rooted young plant, summer*.—About 13 days at 20° C.

*Time to produce a rooted young plant, winter*.—About 15 days at 20° C.

*Root description*.—Fine, fibrous; light brown in color.

*Rooting habit*.—Freely branching, moderately dense.

Plant description:

*Appearance/growth habit*.—Herbaceous daisy-type cut flower that is typically grown as a spray-type; vigorous growth habit.

*Flowering stem description*.—Aspect: Erect. Strength: Strong. Length: About 85 cm. Spray diameter: About 25 cm. Stem diameter: About 7 mm to 8 mm. Internode length: About 1.5 cm to 2.5 cm. Texture: Finely pubescent; longitudinally ridged. Color: Close to 146C.

*Foliage description*.—Arrangement: Alternate; simple. Length: About 6.5 cm to 13 cm. Width: About 5.5 cm to 10 cm. Apex: Mucronulate. Base: Attenuate. Margin: Palmately lobed, serrate; sinuses parallel to convergent. Texture, upper and lower surfaces: Pubescent, slightly rough; veins prominent on lower surface. Venation pattern: Pinnate, reticulate. Color: Developing leaves, upper surface: Close to 137B. Developing leaves, lower surface: Lighter than 147B. Fully developed leaves, upper surface: Close to 147A; venation, close to 146B. Fully developed leaves, lower surface: Close to 147B; venation, close to 147B. Petiole: Length: About 1.5 cm to 3.5 cm. Diameter: About 5 mm. Texture, upper and lower surfaces: Slightly rough. Color, upper surface: Close to 146C. Color, lower surface: Close to 146B.

Inflorescence description:

*Appearance*.—Daisy-type inflorescence form with oval to obovate-shaped ray florets and tubular disc florets; inflorescences borne perpendicular to axillary laterals (peduncles); ray and disc florets develop acropetally on a capitulum.

*Fragrance*.—Moderately fragrant.

*Flowering response*.—Under natural conditions, plant flower in the autumn/winter in the Northern Hemisphere; at other times of the year, inflorescence initiation and development can be induced under short day/long night conditions (at least 13.5 hours of darkness); uniform flowering response; plants exposed to twelve days of long day/short night conditions after planting followed by photoinductive short day/long night conditions flower about 49 days later when grown as a spray-type.

*Postproduction longevity*.—In an interior environment, inflorescences and foliage will maintain good color and substance for about 19 days; inflorescences persistent.

*Quantity of inflorescences*.—Grown as a spray type, about 10 to 15 inflorescences develop.

*Inflorescence size*.—Diameter: About 7 cm. Depth (height): About 3 cm. Disc diameter: About 1.5 cm. Receptacle height: About 4 mm to 5 mm. Receptacle diameter: About 7 mm to 8 mm. Receptacle color: Close to 145B.

*Inflorescence buds*.—Shape: Flattened spherical. Height: About 2 mm. Diameter: About 4 mm. Color: Close to 137C and 149D.

*Ray florets*.—Length: About 2.8 cm to 3.5 cm. Width: About 1 cm to 1.4 cm. Shape: Oval to obovate. Apex: Rounded or emarginate. Base: Fused. Margin: Entire. Texture, upper and lower surfaces: Smooth, glabrous; satiny. Number per inflorescence: About 25 arranged in about one to two whorls. Aspect: About 45° from horizontal. Color: When opening and fully opened, upper surface: Close to NN155D. When opening and fully opened, lower surface: Close to NN155D.

*Disc florets*.—Shape: Fused tubular, erect and elongated. Apex: Dentate. Length: About 6 mm. Diameter: About 1 mm. Number per inflorescence: About 250, massed at the center of the receptacle. Color: When opening: Apex: Close to 144C. Mid-section:

Close to 13B. Base: Close to 145D. Fully opened: Apex: Close to N144B. Mid-section: Close to 145C. Base: Close to 145D.

*Involucral bracts*.—Length: About 6 mm to 9 mm. Width: About 2 mm to 5 mm. Shape: Oval to ovate. Apex: Rounded. Base: Rounded to truncate. Margin: Entire. Texture, upper and lower surfaces: Smooth, glabrous. Number per inflorescence: About 35 arranged in about three whorls. Color, upper surface: Close to 137C. Color, lower surface: Close to 137B.

*Peduncles*.—Length, fourth peduncle: About 13 cm to 14 cm. Length, seventh peduncle: About 16 cm to 18 cm. Diameter: About 3 mm. Strength: Strong. Angle: About 30° from the flowering stem axis. Texture: Pubescent. Color: Close to 146B.

*Reproductive organs*.—Androecium: Not observed. Gynoecium (Present on both ray and disc florets): Stigma shaped: Lobed. Stigma color: Yellow. Style length: About 5 mm. Style color: Green.

*Seed/fruit*.—Seed and fruit production have not been observed.

Disease/pest resistance: Plants of the new *Chrysanthemum* have been observed to be tolerant to White Rust. Resistance to pests and other pathogens common to *Chrysanthemums* has not been observed.

It is claimed:

1. A new and distinct *Chrysanthemum* plant named 'Astec' as illustrated and described.

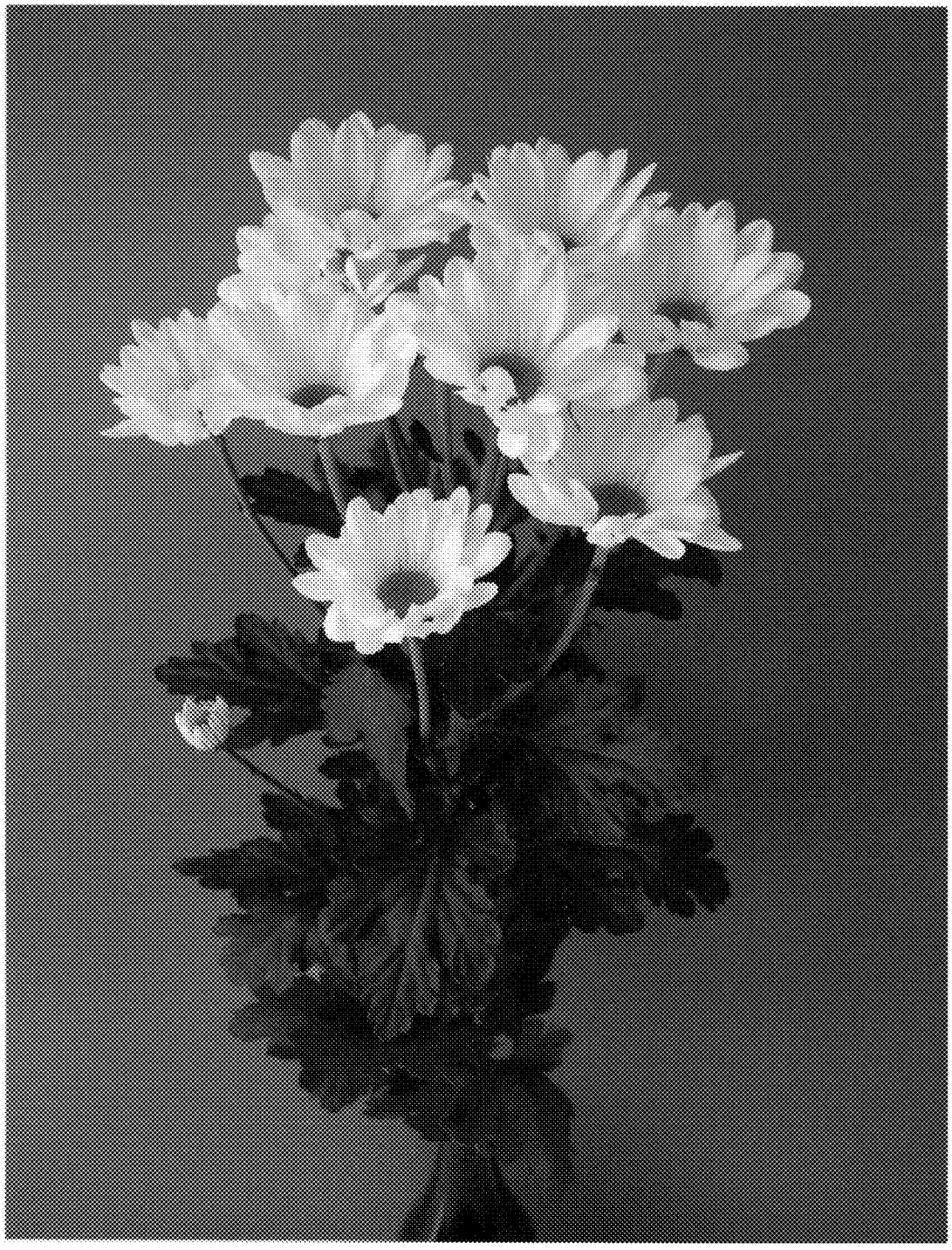

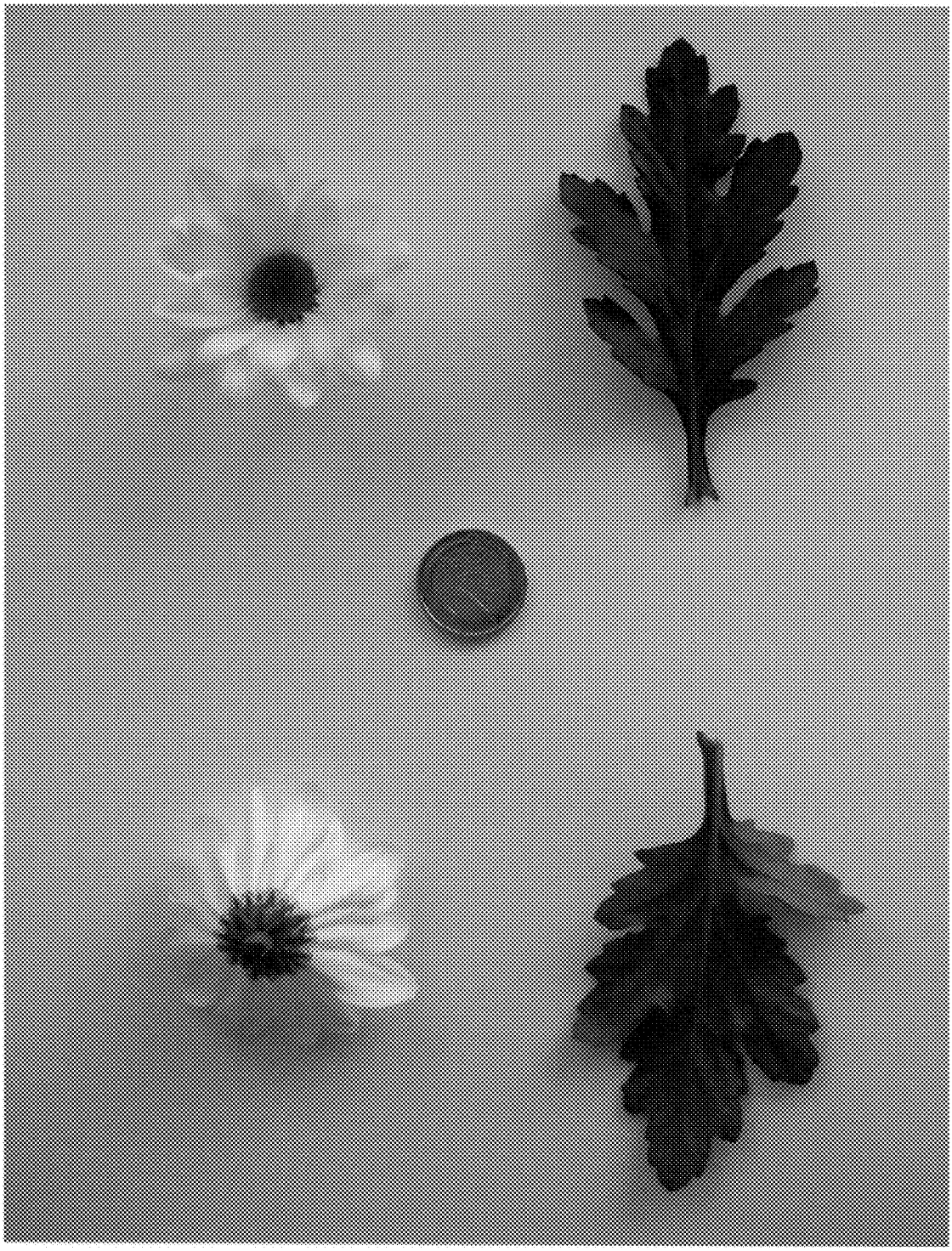

* * * * *